(12) United States Patent
Mathe et al.

(10) Patent No.: US 10,702,479 B2
(45) Date of Patent: Jul. 7, 2020

(54) PHARMACEUTICAL FORMULATION COMPRISING SEMBRAGILINE

(71) Applicant: Hoffmann-La Roche Inc., Little Falls, NJ (US)

(72) Inventors: Zoltan Mathe, Basel (CH); Lene Maurer, Basel (CH); Valérie Verhoeven, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 129 days.

(21) Appl. No.: 15/715,638

(22) Filed: Sep. 26, 2017

(65) Prior Publication Data

US 2018/0042853 A1     Feb. 15, 2018

Related U.S. Application Data

(63) Continuation of application No. PCT/EP2016/056304, filed on Mar. 23, 2016.

(30) Foreign Application Priority Data

Mar. 27, 2015 (EP) .................................... 15161286

(51) Int. Cl.
   *A61K 9/20*      (2006.01)
   *A61K 31/402*    (2006.01)
   *A61K 31/03*     (2006.01)
   *A61K 31/05*     (2006.01)
   *A61K 31/165*    (2006.01)
   *A61K 31/4015*   (2006.01)
   *A61K 47/32*     (2006.01)
   *A61K 47/38*     (2006.01)
   *A61K 9/28*      (2006.01)

(52) U.S. Cl.
CPC ............ *A61K 9/205* (2013.01); *A61K 9/2018* (2013.01); *A61K 9/2031* (2013.01); *A61K 9/2054* (2013.01); *A61K 9/2059* (2013.01); *A61K 31/03* (2013.01); *A61K 31/05* (2013.01); *A61K 31/165* (2013.01); *A61K 31/402* (2013.01); *A61K 31/4015* (2013.01); *A61K 47/32* (2013.01); *A61K 47/38* (2013.01); *A61K 9/2866* (2013.01)

(58) Field of Classification Search
None
See application file for complete search history.

(56) References Cited

U.S. PATENT DOCUMENTS

2004/0224916 A1* 11/2004 Dahl .................... A61K 31/513
                                                                                                         514/47

FOREIGN PATENT DOCUMENTS

WO     2004/026825 A1     4/2004

OTHER PUBLICATIONS

ISR for PCT/EP2016/056304 (dated Apr. 28, 2016).
Ivan Berlin et al., "A selective reversible monoamine oxidase B inhibitor in smoking cessation: effects on its own and in association with transdermal nicotine patch" Psychopharmacology 223(1):89-98 (Mar. 27, 2012).

* cited by examiner

*Primary Examiner* — Jake M Vu

(57) ABSTRACT

The invention relates to pharmaceutical formulation in form of a film-coating tablet comprising sembragiline or a salt thereof.

5 Claims, 2 Drawing Sheets

PHARMACEUTICAL FORMULATION COMPRISING SEMBRAGILINE

CROSS REFERENCE TO RELATED APPLICATIONS

Figure 1:
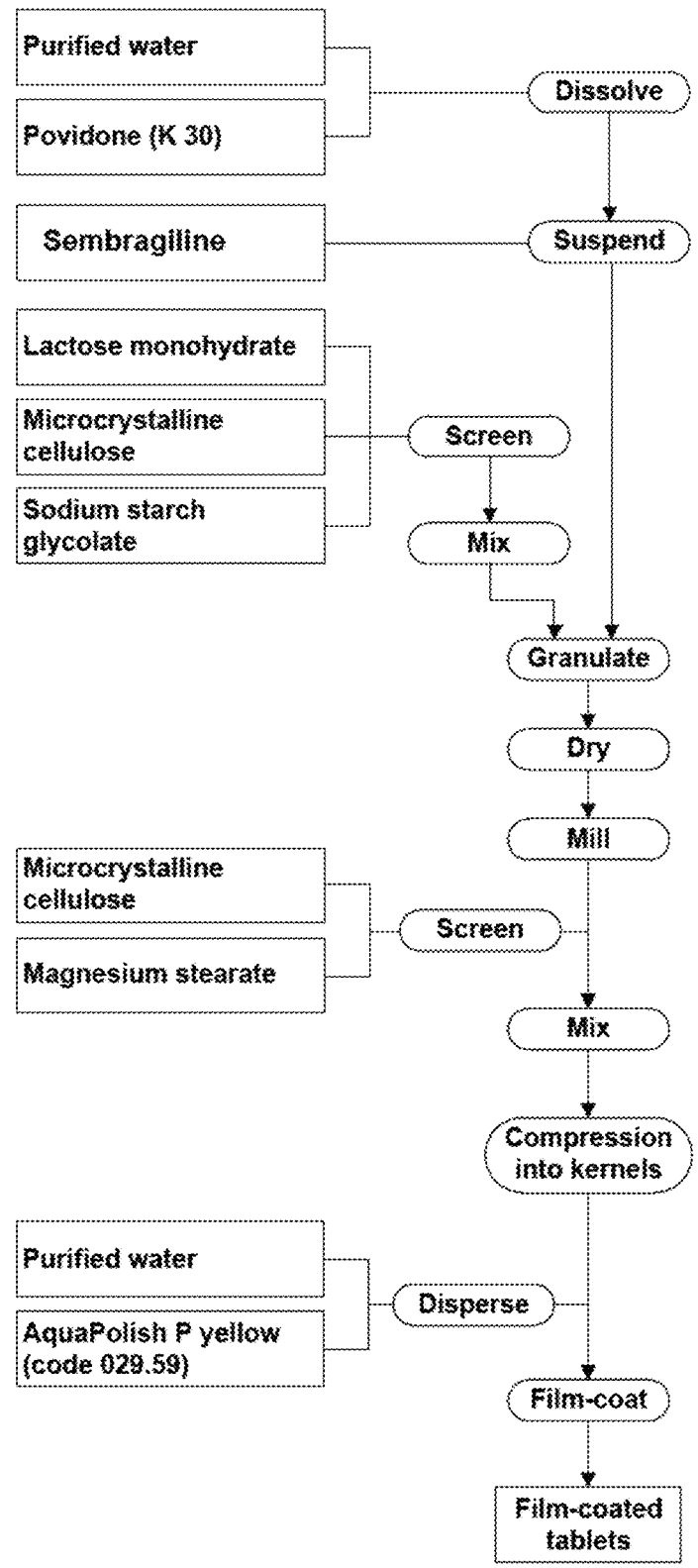

This application is a continuation of PCT/EP2016/056304 filed Mar. 23, 2016 which claims the benefit of priority to European Patent Application No. 15161286.8 filed Mar. 27, 2015 the content of both of which are incorporated by reference in their entirety.

FIELD OF THE INVENTION

The invention relates to a pharmaceutical formulation and in particular to a pharmaceutical formulation comprising Sembragiline or a salt thereof.

BACKGROUND OF THE INVENTION

Sembragiline (N-[(3S)-1-[4-[(3-fluorophenyl)methoxy]phenyl]-5-oxo-pyrrolidin-3-yl]acetamide has previously been described in the art. WO 2004/026825[1], WO 2006/097197[2] and WO 2006/097270[3] relate to methods for preparing enantiomerically pure 4-pyrrolidinophenylbenzyl ether derivatives. Sembragiline is a Monoamine oxidase-B type (MAO-B) inhibitor.

Alzheimer's Disease is a brain disease that slowly destroys memory and thinking skills, up to loss of the ability to carry out the simplest tasks. It is the most common cause of dementia among older people. Mild Alzheimer's Disease manifests itself in memory loss and small changes in other cognitive abilities, e.g. getting lost, trouble handling money and managing daily tasks, having some mood and personality changes, etc. In the stage of Moderate Alzheimer's Disease, the control of language, reasoning, sensory processing, and conscious thought are impacted. Memory loss and confusion grow worse, e.g. patients have problems recognizing family and friends and become unable to learn new things, etc. hallucinations, delusions, and paranoia may occur. Severe Alzheimer's Disease is the final stage. Patients cannot communicate anymore and are completely dependent.

MAO-B is involved in Alzheimer's Disease etiology. MAO-B activity is increased in several regions of the brain from an early stage and this is maintained throughout the course of the disease. MAO-B activity is believed to be involved in the production of toxic reactive oxygen species, which are thought to contribute to the pathogenesis of Alzheimer's Disease.

Object of the present invention is to provide stable tablet formulations of different strengths suitable for oral administration of Sembragiline and methods to prepare the same. These formulations have a better manufacturability and performance as previously described formulations.

Definitions

The following definitions of the general terms used in the present description apply irrespectively of whether the terms in question appear alone or in combination with other groups.

DETAILED DESCRIPTION OF THE INVENTION

Present invention provides stable tablet formulations of different strengths suitable for oral administration of sembragiline.

In particular, sembragiline has been formulated as 1 mg and 5 mg film-coated, immediate-release tablets for oral administration. The 1 mg and 5 mg tablets are manufactured by aqueous fluid bed granulation, mixing, tableting, and coating.

Present film-coated tablets use a 4:1 ratio of lactose monohydrate: microcrystalline cellulose (MCC) in the internal phase to reach optimal granule particle sizes and therewith optimal flow properties. Present tablets contain 4% povidone K30 as binder and 9.33% MCC in the external phase as filler. The level of sodium starch glycolate in present tablets is 2.5% that leads to satisfactory dissolution rates of the tablets. The level of magnesium stearate in present tablets is 0.67% (film-coated tablets) that leads to a satisfactory lubrication level.

Sembragiline (CAS RN 676479-06-4) has the following structure

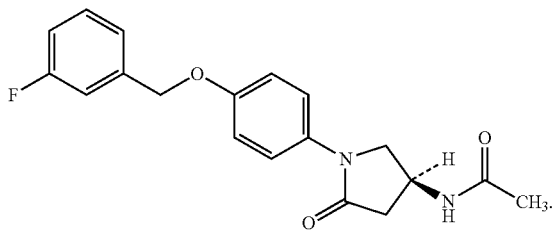 [SMILES: CC(=O)N[C@H]1CC(=O)N(c2ccc(OCc3cccc(F)c3)cc2)C1]

The term "disintegrant" refers to excipients that expand and dissolve when wet causing the tablet to break apart in the body and release the active ingredient for absorption. Examples include cross-linked polymers like crospovidone, croscarmellose sodium etc. and modified starches like sodium starch glycolate. A specific example is Primojel.

The term "filler" refers to excipients that fill out the size of a tablet by increasing the bulk volume. Fillers make it possible for the final product to have the proper volume for patient handling. Examples of fillers are plant cellulose, lactose, starch, mannitol, etc. Specific examples are lactose monohydrate like Pharmatose 200M and microcrystalline cellulose (MCC) like Avicel PH101, Avicel PH102 and the like.

The term "binder" refers to excipients that hold the ingredients in a tablet together. Binders ensure that tablets and granules can be formed with required mechanical strength. Examples of binders are, polyvinlypyrrolidon (PV), hydroxypropyl methylcellulose (HPMC), hydroxypropylcellulose (HPC), cellulose, etc., sugar alcohols like sorbitol, proteins like gelatin and polymers like PVP, e.g. copovidone (PVP/VA 64)., PEG, etc. A specific example is Povidone K30.

The term "lubricant" refers to excipients that prevent ingredients from clumping together and from sticking to the tablet punches or capsule filling machine. Lubricants also ensure that tablet formation and ejection can occur with low fraction between active ingredient and wall. Examples of lubricants are minerals like talc or silica and fats like stearin, magnesium stearate, etc. A specific example is magnesium stearate.

The term "coating agent" refers functional coating agents that is a group of substances that provides a coating to provide a barrier to protect drugs from e.g. the PH environment of the stomach, and non-functional coating agents. A specific example of a non-functional coating agent is Aqua Polish P yellow (029.59).

One embodiment of present invention relates to a pharmaceutical formulation in form of a film-coating tablet comprising sembragiline or a salt thereof.

A specific embodiment of present invention relates to a pharmaceutical formulation as described herein, consisting of an internal phase that comprises sembragiline, an external phase and a coating phase.

A specific embodiment of present invention relates to a pharmaceutical formulation as described herein, wherein the internal phase are granules comprising sembragiline, fillers, disintegrant and binder.

A specific embodiment of present invention relates to a pharmaceutical formulation as described herein, wherein the fillers are lactose monohydrate and microcrystalline cellulose.

A specific embodiment of present invention relates to a pharmaceutical formulation as described herein, wherein the disintegrant is sodium starch glycolate.

A specific embodiment of present invention relates to a pharmaceutical formulation as described herein, wherein the binder is polyvinylpyrrolidone.

A specific embodiment of present invention relates to a pharmaceutical formulation as described herein, wherein the external phase comprises filler and lubricant.

A specific embodiment of present invention relates to a pharmaceutical formulation as described herein, wherein the filler of the external phase is microcrystalline cellulose.

A specific embodiment of present invention relates to a pharmaceutical formulation as described herein, wherein the lubricant is magnesium stearate.

A specific embodiment of present invention relates to a pharmaceutical formulation as described herein, wherein the coating agent is a non-functional coating agent.

A specific embodiment of present invention relates to a pharmaceutical formulation as described herein that is

| Substance | mg/tablet | % (w/w) |
|---|---|---|
| Internal Phase | | |
| Sembragiline | 1.00 | 0.67 |
| Lactose Monohydrate | 99.40 | 66.27 |
| Microcrystalline cellulose | 24.85 | 16.57 |
| Sodium starch glycolate | 3.75 | 2.50 |
| Polyvinylpyrrolidone | 6.00 | 4.00 |
| External Phase | | |
| Microcrystalline cellulose | 14.00 | 9.33 |
| Magnesium stearate | 1.00 | 0.67 |
| Coating Phase | | |
| Coating agent | 5.00 | 3.33 |

A specific embodiment of present invention relates to a pharmaceutical formulation as described herein that is

| Substance | mg/tablet | % (w/w) |
|---|---|---|
| Internal Phase | | |
| Sembragiline | 5.00 | 3.33 |
| Lactose Monohydrate | 96.20 | 64.13 |
| Microcrystalline cellulose | 24.05 | 16.03 |
| Sodium starch glycolate | 3.75 | 2.50 |
| Polyvinylpyrrolidone | 6.00 | 4.00 |
| External Phase | | |
| Microcrystalline cellulose | 14.00 | 9.33 |
| Magnesium stearate | 1.00 | 0.67 |
| Coating Phase | | |
| Coating agent | 5.00 | 3.33 |

A specific embodiment of present invention relates to a pharmaceutical formulation as described herein that has the following dissolution profile

| | |
|---|---|
| After 5 min | 53% (45/63/7.2) |
| After 10 min | 91% (88/94/2.3) |
| After 15 min | 99% (95/107/4.2) |
| After 20 min | 102% (99/110/4.4) |
| After 30 min | 103% (100/111/4.2) |
| After 45 min | 103% (101/113/4.7) |
| After 60 min | 103% (101/114/5.0) |

A specific embodiment of present invention relates to a pharmaceutical formulation as described herein that has the following dissolution profile

| | |
|---|---|
| After 5 min | 39% (32/48/5.4) |
| After 10 min | 74% (72/78/2.3) |
| After 15 min | 89% (87/91/1.6) |
| After 20 min | 95% (94/97/1.1) |
| After 30 min | 98% (97/99/0.7) |
| After 45 min | 100% (99/100/0.5) |
| After 60 min | 101% (100/101/0.4) |

Figure 2:
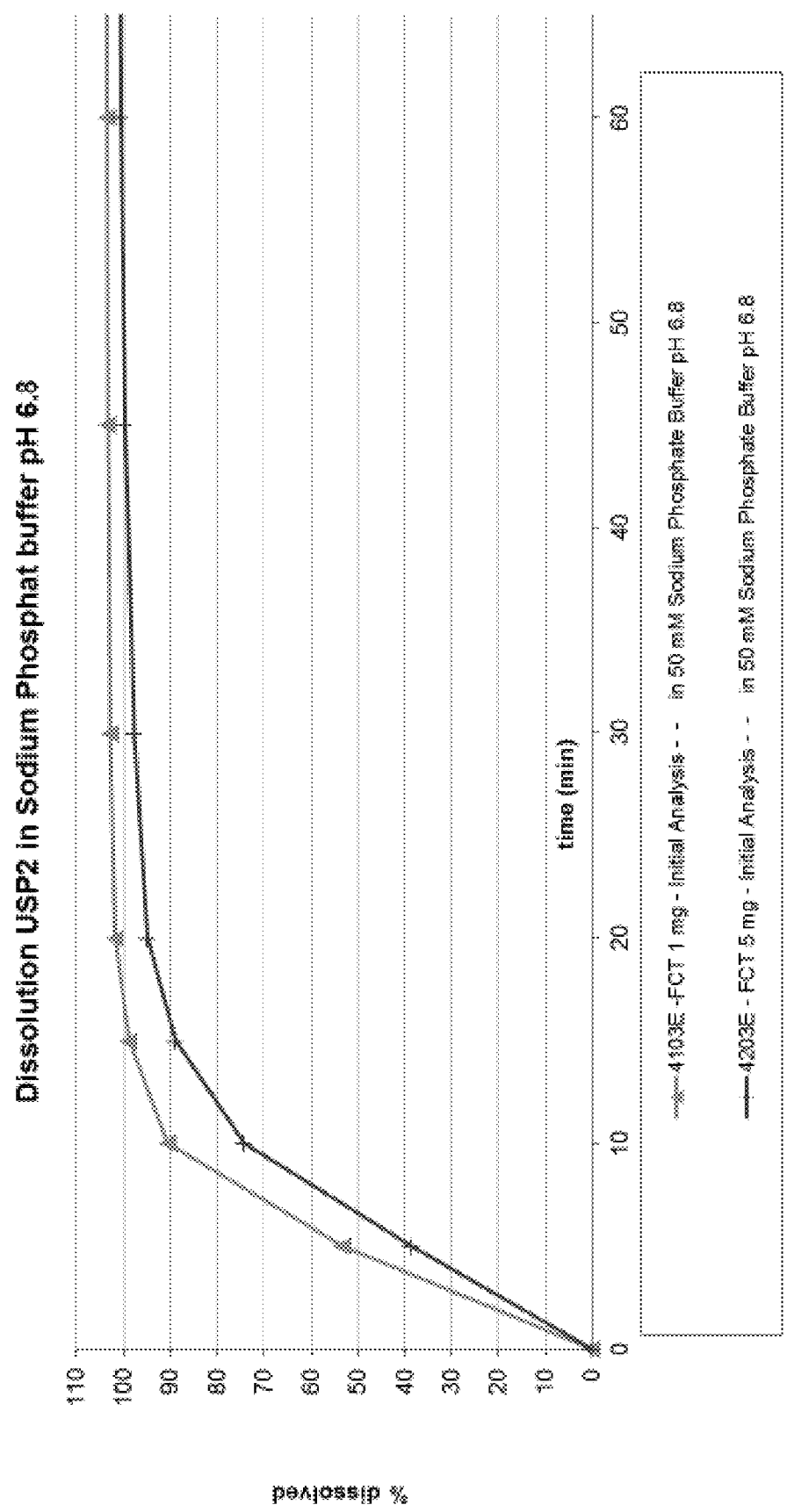

A specific embodiment of present invention relates to a pharmaceutical formulation as described herein that has the dissolution profile as shown in FIG. 2.

A specific embodiment of present invention relates to a pharmaceutical formulation as described herein, for the treatment of Alzheimer's Disease.

A specific embodiment of present invention relates to a pharmaceutical formulation as described herein, obtainable by the process comprising the steps of aqueous fluid bed granulation, mixing, tableting, and coating.

A specific embodiment of present invention relates to a pharmaceutical formulation as described herein, obtainable by the process as shown in FIG. 1.

A specific embodiment of present invention relates to a pharmaceutical formulation as described herein, obtainable by the process comprising the steps
1. Povidone is dissolved in purified water and the milled Sembragiline is then suspended in the resulting solution.
2. After screening, the lactose monohydrate, MCC, and sodium starch glycolate are mixed in a fluid bed granulator.
3. The mixed powder from step 2 is granulated with the suspension from step 1.
4. The granulate from step 3 is dried and then milled.
5. The milled granulate from step 4 is mixed with screened MCC and magnesium stearate.
6. The final blend from step 5 is compressed into tablet cores.
7. The cores from step 6 are coated with the film-coating mixture in order to obtain film-coated tablets.

A specific embodiment of present invention relates to a pharmaceutical formulation as described herein, wherein the sembragiline is in crystalline form.

A specific embodiment of present invention relates to a pharmaceutical formulation as described herein, wherein the pharmaceutical formulation is a tablet.

A specific embodiment of present invention relates to a tablet comprising a pharmaceutical formulation as described herein.

A specific embodiment of present invention relates to a pharmaceutical formulation as described herein, for use as medicament for the treatment of Alzheimer's Disease.

A specific embodiment of present invention relates to a pharmaceutical formulation as described herein, for the treatment of Alzheimer's Disease.

A specific embodiment of present invention relates to a method for the treatment of Alzheimer's Disease, comprising the step of administering a pharmaceutical formulation as described herein to a patient in need thereof.

A specific embodiment of present invention relates to a pharmaceutical formulation as described herein, which is administered once daily.

FIGURES

FIG. 1: Manufacturing Process of film-coated tablets
FIG. 2: Dissolution in Sodium Phosphat buffer pH 6.8

EXPERIMENTAL PART

The following experiments are provided for illustration of the invention. They should not be considered as limiting the scope of the invention, but merely as being representative thereof.

Manufacturing of the Tablets
1. Povidone K30 is dissolved in purified water and the milled Drug Substance Sembragiline is then suspended in the resulting solution.
2. After screening, the lactose monohydrate, MCC, and sodium starch glycolate are mixed in a fluid bed granulator.
3. The mixed powder from step 2 is granulated with the suspension from step 1.
4. The granulate from step 3 is dried and then milled.
5. The milled granulate from step 4 is mixed with screened MCC and magnesium stearate.
6. The final blend from step 5 is compressed into tablet cores.
7. The cores from step 6 are coated with the film-coating mixture in order to obtain film-coated tablets.

Pharmaceutical Formulations

Example 1.1: 1 mg

| Substance | mg/tablet | % (w/w) |
|---|---|---|
| Internal Phase | | |
| Sembragiline | 1.00 | 0.67 |
| Lactose monohydrate | 99.40 | 66.27 |
| MCC | 24.85 | 16.57 |
| Sodium starch glycolate | 3.75 | 2.50 |
| Povidone K30 | 6.00 | 4.00 |
| External Phase | | |
| MCC | 14.00 | 9.33 |
| Magnesium stearate | 1.00 | 0.67 |
| Coating Phase | | |
| Aqua Polish P Yellow (029.59) | 5.00 | 3.33 |

Example 1.2: 1 mg

| Substance | mg/tablet | % (w/w) |
|---|---|---|
| Internal Phase | | |
| Sembragiline | 1.00 | 0.67 |
| Pharmatose 200M | 99.40 | 66.27 |
| Avicel PH101 | 24.85 | 16.57 |
| Primojel | 3.75 | 2.50 |
| Povidone K30 | 6.00 | 4.00 |
| External Phase | | |
| Avicel PH102 | 14.00 | 9.33 |
| Magnesium stearate | 1.00 | 0.67 |
| Coating Phase | | |
| Aqua Polish Yellow (029.59) | 5.00 | 3.33 |

Example 2.1: 5 mg

| Substance | mg/tablet | % (w/w) |
|---|---|---|
| Internal Phase | | |
| Sembragiline | 5.00 | 3.33 |
| Lactose monohydrate | 96.20 | 64.13 |
| MCC | 24.05 | 16.03 |
| Sodium starch glycolate | 3.75 | 2.50 |
| Povidone K30 | 6.00 | 4.00 |
| External Phase | | |
| MCC | 14.00 | 9.33 |
| Magnesium stearate | 1.00 | 0.67 |
| Coating Phase | | |
| Aqua Polish P Yellow (029.59) | 5.00 | 3.33 |

Example 2.2: 5 mg

| Substance | mg/tablet | % (w/w) |
|---|---|---|
| Internal Phase | | |
| Sembragiline | 5.00 | 3.33 |
| Pharmatose 200M | 96.20 | 64.13 |
| Avicel PH101 | 24.05 | 16.03 |
| Primojel | 3.75 | 2.50 |
| Povidone K30 | 6.00 | 4.00 |
| External Phase | | |
| Avicel PH102 | 14.00 | 9.33 |
| Magnesium stearate | 1.00 | 0.67 |
| Coating Phase | | |
| Aqua Polish P Yellow (029.59) | 5.00 | 3.33 |

Solubility

| Media (at 37° C.) | Solubility of Sembragiline After 4 h (mg/mL) | Solubility of Sembragiline 250 mL | Dose Solubility Ratio 1 mg | Dose Solubility Ratio 5 mg |
|---|---|---|---|---|
| Water | 0.04 | 10 mg | 25 | 125 |
| pH 1, HCl 0.1N | 0.04 | 10 mg | 25 | 125 |
| pH 4.5, 50 mM acetate buffer | 0.04 | 10 mg | 25 | 125 |
| pH 6.8, 50 mM phosphate buffer | 0.04 | 10 mg | 25 | 125 |
| pH 7.5, 50 mM phosphate buffer | 0.04 | 10 mg | 25 | 125 |

Stability of Tablets

TABLE 1

Stability Report Film-coated tablets 1 mg in HDPE Bottles without desiccant

| Tests | Specifications | 6 Months 5° C. | 6 Months 30° C./75% r.h. | 6 Months 40° C./75% r.h. |
|---|---|---|---|---|
| Content per Tablet by HPLC | 90.0%-110.0% | 100.0% | 100.0% | 99.3% |
|  | 0.9 mg-1.1 mg | 1.0 mg | 1.0 mg | 1.0 mg |
| Degradation Products |  |  |  |  |
| X | max 0.15% | ≤0.05% | ≤0.05% | ≤0.05% |
| Unspecified, each | max 0.15% | ≤0.05% | ≤0.05% | 0.10% (RRT 0.75) |
| Unspecified, total | max 2.0% | ≤0.05% | ≤0.05% | 0.1% |
| Total of all degradation products | max 2.0% | ≤0.05% | ≤0.05% | 0.1% |
| Content Uniformity | corresponds | corresponds | — | — |
| Mean(min/max/Srel/AV/nb of units) |  | 100.7 (100.2/101.4/0.4/0.9/6) | — | — |
| Dissolution Q = 80% after 45 min | Corresponds to S1 or S2 or S3 | Corresponds to S1 | Corresponds to S1 | Corresponds to S1 |
| After 5 min | Report Mean (min/max/Srel) | 53% (43/66/9.4) | 60% (47/72/4.1) | 59% (54/62/3.5) |
| After 10 min | Report Mean (min/max/Srel) | 84% (80/87/2.4) | 87% (80/91/4.1) | 86% (84/92/2.8) |
| After 15 min | Report Mean (min/max/Srel) | 92% (90/93/1.1) | 95% (92/97/2.0) | 95% (92/100/2.8) |
| After 20 min | Report Mean (min/max/Srel) | 95% (93/97/1.2) | 98% (97/99/0.8) | 99% (96/102/2.4) |
| After 30 min | Report Mean (min/max/Srel) | 98% (95/100/1.9) | 100% (100/102/0.7) | 101% (98/104/2.2) |
| After 45 min | Report Mean (min/max/Srel) | 100% (96/102/2.2) | 102% (101/103/0.6) | 102% (99/105/2.4) |
| After 60 min | Report Mean (min/max/Srel) | 101% (97/102/2.2) | 102% (101/103/0.6) | 104% (102/107/2.4) |
| Water Content | Report | 5.0% | 5.4% | 5.6% |
| Disintegration | Report | 4 min | 4 min | 4 min |
| Average mass of 20 Tablets | Report | 155.4 mg | 156.3 mg | 156.9 mg |
| Hardness | Report | 11.8 kP | 10.6 kP | 11.5 kP |

TABLE 2

| Tests | Specifications | 6 Months 5° C. | 6 Months 30° C./75% r.h. | 6 Months 40° C./75% r.h. |
|---|---|---|---|---|
| Appearance | Yellow round coated tablets | Yellow round coated tablets | Yellow round coated tablets | Yellow round coated tablets |
| Content per Tablet by HPLC | 90.0%-110.0% | 98.2% | 98.6% | 98.5% |
|  | 4.5 mg-5.5 mg | 4.9 mg | 4.9 mg | 4.9 mg |
| Degradation Products |  |  |  |  |
| X | max 0.15% | ≤0.05% | ≤0.05% | ≤0.05% |
| Unspecified, each | max 0.15% | ≤0.05% | ≤0.05% | ≤0.05% |
| Unspecified, total | max 2.0% | ≤0.05% | ≤0.05% | ≤0.05% |
| Total of all degradation products | max 2.0% | ≤0.05% | ≤0.05% | ≤0.05% |
| Content Uniformity | corresponds | corresponds | — | — |
|  | Mean(min/max/Srel/AV/nb of units) | 101.2 (100.4/102.4/0.6/1.4/6) | — | — |
| Dissolution Q = 80% after 45 min | Corresponds to S1 or S2 or S3 | Corresponds to S1 | Corresponds to S1 | Corresponds to S1 |
| After 5 min | Report Mean (min/max/Srel) | 55% (45/66/7.9) | 48% (39/53/5.2) | 51% (44/57/2.9) |
| After 10 min | Report Mean (min/max/Srel) | 82% (76/89/4.7) | 81% (75/85/3.3) | 81% (78/86/2.9) |
| After 15 min | Report Mean (min/max/Srel) | 89% (84/93/3.6) | 92% (88/95/2.8) | 90% (88/94/2.0) |
| After 20 min | Report Mean (min/max/Srel) | 91% (87/95/3.1) | 96% (94/98/1.8) | 93% (93/94/0.5) |
| After 30 min | Report Mean (min/max/Srel) | 94% (89/97/2.8) | 99% (97/100/1.3) | 97% (96/98/1.0) |
| After 45 min | Report Mean (min/max/Srel) | 96% (91/98/2.7) | 100% (99/101/1.3) | 99% (98/100/0.9) |
| After 60 min | Report Mean (min/max/Srel) | 97% (93/99/2.5) | 100% (99/101/1.1) | 100% (99/101/0.8) |
| Water Content | Report | 4.9% | 5.2% | 5.5% |
| Disintegration | Report | 4 min | 4 min | 3 min |
| Average mass of 20 Tablets | Report | 155.5 mg | 156.7 mg | 157.3 mg |
| Hardness | Report | 11.8 kP | 10.9 kP | 11.0 kP | wherein degradation product X has the following structure:

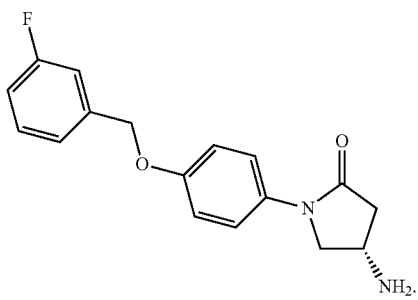

X

After 6 months at 40° C./75% r.h. all analytical tests are well within the specifications. Sembragiline film-coated tablets are very stable.

Dissolution Experimental Conditions:

| Apparatus | Ph. Eur. paddle apparatus (U.S.P. Apparatus 2) |
|---|---|
| Dissolution Medium | 50 mM Sodium phosphate buffer, pH 6.8 |
| Dissolution Volume | 900 mL |
| Temperature | 37° C. ± 0.5° C. |
| Shaft Rotation Speed | 50 ± 2 rpm |
| Sample | 6 × 1 Tablet |
| Sampling Profile | After 5, 10, 15, 20, 30, 45, 60 minutes |
| Method of Analysis | HPLC with UV detection at 250 nm |

| Tests | 4103E -FCT 1 mg - Initial Analysis | 4203E - FCT 5 mg - Initial Analysis - - |
|---|---|---|
| Dissolution Q = 80% after 45 min | Corresponds to S1 or S2 or S3 Mean(min/max/Srel/AV/nb of units) | Corresponds to S1 Mean(min/max/Srel/AV/nb of units) |
| After 5 min | 53% (45/63/7.2) | 39% (32/48/5.4) |
| After 10 min | 91% (88/94/2.3) | 74% (72/78/2.3) |
| After 15 min | 99% (95/107/4.2) | 89% (87/91/1.6) |

-continued

| Tests | 4103E -FCT 1 mg - Initial Analysis | 4203E - FCT 5 mg - Initial Analysis - - |
|---|---|---|
| After 20 min | 102% (99/110/4.4) | 95% (94/97/1.1) |
| After 30 min | 103% (100/111/4.2) | 98% (97/99/0.7) |
| After 45 min | 103% (101/113/4.7) | 100% (99/100/0.5) |
| After 60 min | 103% (101/114/5.0) | 101% (100/101/0.4) |

The pharmaceutical composition has a rapid dissolution, e.g. at least 85% of the dose is dissolved within 30 min in 900 mL of pH 6.8 buffer which is consistent with an immediate release profile.

[1] WO 2004/026825
[2] WO 2006/097197
[3] WO 2006/097270

The invention claimed is:

1. A pharmaceutical formulation in form of a film-coating tablet comprising sembragiline or a salt thereof, that is:

| Substance | mg/tablet | % (w/w) |
|---|---|---|
| Internal Phase | | |
| Sembragiline | 1.00 | 0.67 |
| Lactose Monohydrate | 99.40 | 66.27 |
| Microcrystalline cellulose | 24.85 | 16.57 |
| Sodium starch glycolate | 3.75 | 2.50 |
| Polyvinylpyrrolidone | 6.00 | 4.00 |
| External Phase | | |
| Microcrystalline cellulose | 14.00 | 9.33 |
| Magnesium stearate | 1.00 | 0.67 |
| Coating Phase | | |
| Coating agent | 5.00 | 3.33 |

2. A pharmaceutical formulation according to claim 1 that has the following dissolution profile

| After 5 min | 53% (45/63/7.2) |
|---|---|
| After 10 min | 91% (88/94/2.3) |
| After 15 min | 99% (95/107/4.2) |
| After 20 min | 102% (99/110/4.4) |
| After 30 min | 103% (100/111/4.2) |
| After 45 min | 103% (101/113/4.7) |
| After 60 min | 103% (101/114/5.0) |

3. A pharmaceutical formulation in form of a film-coating tablet comprising sembragiline or a salt thereof, that is:

| Substance | mg/tablet | % (w/w) |
|---|---|---|
| Internal Phase | | |
| Sembragiline | 5.00 | 3.33 |
| Lactose Monohydrate | 96.20 | 64.13 |
| Microcrystalline cellulose | 24.05 | 16.03 |
| Sodium starch glycolate | 3.75 | 2.50 |
| Polyvinylpyrrolidone | 6.00 | 4.00 |
| External Phase | | |
| Microcrystalline cellulose | 14.00 | 9.33 |
| Magnesium stearate | 1.00 | 0.67 |
| Coating Phase | | |
| Coating agent | 5.00 | 3.33 |

4. A pharmaceutical formulation according to claim 3 that has the following dissolution profile

| After 5 min | 39% (32/48/5.4) |
|---|---|
| After 10 min | 74% (72/78/2.3) |
| After 15 min | 89% (87/91/1.6) |
| After 20 min | 95% (94/97/1.1) |
| After 30 min | 98% (97/99/0.7) |
| After 45 min | 100% (99/100/0.5) |
| After 60 min | 101% (100/101/0.4) |

5. A pharmaceutical formulation according to claim 1, obtainable by the process comprising the steps
   1. Povidone is dissolved in purified water and the milled Sembragiline is then suspended in the resulting solution
   2. After screening, the lactose monohydrate, MCC, and sodium starch glycolate are mixed in a fluid bed granulator
   3. The mixed powder from step 2 is granulated with the suspension from step 1
   4. The granulate from step 3 is dried and then milled
   5. The milled granulate from step 4 is mixed with screened MCC and magnesium stearate
   6. The final blend from step 5 is compressed into tablet cores
   7. The cores from step 6 are coated with the film-coating mixture in order to obtain film-coated tablets.

* * * * *